United States Patent [19]
Ulrich et al.

[11] 3,983,866
[45] Oct. 5, 1976

[54] PHOTOELECTRIC PULSEMETER

[75] Inventors: Alfred Ulrich, Furth; Georg Naser, Zirndorf, both of Germany

[73] Assignee: Siemens Aktiengesellschaft, Munich, Germany

[22] Filed: Feb. 17, 1972

[21] Appl. No.: 227,175

[30] Foreign Application Priority Data
Nov. 16, 1971 Germany............................ 2156946
Nov. 16, 1971 Germany..................... 7143212[U]

[52] U.S. Cl........................... 128/2.05 P; 128/2.05 T
[51] Int. Cl.²........................................... A61B 5/02
[58] Field of Search.................. 128/2.05 P, 2.05 T, 128/2.06 F, 2.1 Z, 2.05 R, 2 L, 2 B, 2.05 E; 356/39, 40, 41, 42; 250/239, 227

[56] References Cited
UNITED STATES PATENTS

| | | | |
|---|---|---|---|
| 3,040,737 | 6/1962 | Kompelien et al | 128/2.05 E |
| 3,103,214 | 10/1963 | Smith | 128/2.05 P |
| 3,139,086 | 6/1964 | Botsch et al | 128/2.05 P |
| 3,167,658 | 1/1965 | Richter | 128/2.05 P X |
| 3,602,213 | 8/1971 | Howell et al. | 128/2.05 P X |

*Primary Examiner*—Robert W. Michell
*Assistant Examiner*—Lee S. Cohen
*Attorney, Agent, or Firm*—Richards & Geier

[57] ABSTRACT

A photoelectric pulsemeter has an applicator connected to an electrical line and containing a light transmitting source fed from an electrical lamp and a photo-electrical receiver screened upon the application side from the light transmitting source. The invention is particularly characterized in that the applicator is divided and has a carrier containing the application side and the source of transmitting light and a supporting plate removable from the carrier and having the lamp, the receiver and possibly other electrical structural parts and conduits. The lamp and the receiver are so constructed and arranged that when the applicator is mounted they functionally properly adapt themselves to the carrier.

16 Claims, 3 Drawing Figures

PHOTOELECTRIC PULSEMETER

This invention relates to a photoelectric pulsemeter with an applicator connected to an electrical conduit and containing substantially a light transmitting source fed from an electric lamp and a photo-electrical receiver screened on the application side against the source of transmitted light.

In a known pulsemeter of this type the applicator consists of a flat circular plastic part. The plastic part is provided with a side lug piece in which the end of the electrical line to the electrical structural parts is firmly cast. The plastic part is provided on the application side with an annular groove into which is poured a light transmitting mass after the placing of the electrical lamp. The poured mass serves as a light conductor, it is supplied with light from the lamp and acts as a light emitting source for a receiver located in the center of the ring. The receiver which is a photo resistance is also firmly fixed by pouring in the plastic part. A screen consisting of a plastic material which does not transmit light is provided between the receiver and the light emitting source. The screen prevents direct light from the light source from falling upon the receiver. The outer surface of the applicator is flatly polished upon the application side.

The pouring of the electrical structural parts and of the conduit ends into the plastic part has the drawback that in case of a defect of the parts subjected to use, for example, the lamp or the photo resistance, not only the applicator but the entire pulsemeter becomes unuseable and must be replaced by a new one. The same is true in case of a defect in electrical connections. Due to the use of comparatively thin conducting wires they are particularly susceptible to cracking.

An object of the present invention is to improve prior art constructions.

Another object of the present invention is to provide a photoelectrical pulsemeter of the above-described type wherein in case of a defect of an electrical part, including electrical supply conduits to the applicator and from the applicator to the electrical structural parts, the entire pulsemeter will not become unuseable and it will not be necessary to replace it in its entirety. The pulsemeter is to be easily serviceable, so that an arising defect can be quickly and safely localised and the error can be eliminated in a short time and with small expense. Since the pulsemeter is also to be used for intensive examinations in case of emergency a non-specialist should be also able to eliminate the error. It should be also taken into consideration that the amounts of light supplied by the lamp which are very small, as is unavoidable due to the structural necessity of having a small lamp, should be transmitted with the smallest possible losses to the light transmitting source.

Other objects of the present invention will become apparent in the course of the following specification.

In the accomplishment of the objectives of the present invention it was found desirable to divide the applicator into a carrier containing substantially the application side and the light transmitting source and a supporting plate removable from the carrier and carrying the lamp, the receiver and possibly other electrical structural parts and wires. The lamp and the receiver are so constructed and arranged that when the applicator is mounted they properly fit to the carrier. Thus in accordance with the present invention the applicator is divided into a mechanical part and an electrical part. In case of a defect of an electrical structural part or a wire these parts can be quickly located and exchanged without making the entire pulsemeter unuseable. It may be also possible in case of a defect to exchange the entire supporting plate as a structure in an exchange operation.

According to a further embodiment of the present invention the structural parts can be easily and quickly reached by arranging the supporting plate upon the side of the carrier located away from the application side and by covering the outer side of the plate by a cover.

It is advantageous to shape the mounting plate itself as a cover and to use as the mounting plate a conducting plate upon which the electrical construction parts are arranged in a compressed switching arrangement. This simplifies the manufacture of the receiver and avoids disturbances resulting from poor contacting. The replacement of the conducting plate is made easier when the connections to the electrical wiring are constructed as plugs.

If a ring-shaped light conductor is used as the light transmitting source, which is arranged coaxially to the receiver in the carrier, then it is advantageous to provide the light conductor with a recess corresponding to the size of the lamp upon its side located away from the application side. Then after the mounting of the conducting plate upon the applicator the lamp is well placed relatively to the light conductor and the light is uniformly distributed upon the light conductor. Losses upon the transmission side are so small that they can be neglected.

The light conductor consists preferably of a made in advance part of an artificial material, preferably polymethylmethacrylate, and is provided wih a layer which reflects light toward the application side and is located upon its side located away from the application side and possibly upon its side walls. It was found advantageous to steam the light conductor with aluminum to produce this layer.

According to a further embodiment of the present invention the sensitivity of the pulsemeter is further improved by providing a raised portion upon the application surface in the part between the light transmitting source and the receiver. This raised portion can be considered as a raised lever upon that part. This takes into consideration the fact that when the application surface of the pulsemeter is placed upon the skin of a patient and a certain part of the light emitted by the light emitting source drops upon the photoelectrical element, this light portion does not penetrate into the deeper tissue with normally flowing blood, but is conducted along an upper tissue layer located directly below the skin surface and receiving less blood. This light portion is then reflected to the photoelectrical element or is directed by the light emitting source directly upon the photo element as the result of an optical short circuit. This light which can be described as transverse light, is not modulated and cannot be used for a precise pulse measurement. The same applies to direct light, such as daylight or room illumination, falling upon the receiver. When the undesirable transverse or direct light is received, the resistance range of the photo resistance which can be applied for the formation of a signal is shifted so as to make worse the attainable pulse signal.

These drawbacks do not occur in the construction of the present invention due to the raising of the application surface, since when the receiver lies against the skin the part of the skin located between the light transmitting source and the photoelectrical element will be more strongly compressed by the raised portion than the other adjacent skin parts. Then the cross-section of this skin part transmitting the transverse light is greatly diminished and the transmission of transverse light in the upper skin layer which is a very good light transmitter, is prevented to a great extent. The sensitivity and thus also the pulse signals remain practically in their original condition. Furthermore, by increasing the application surface in the part between the light transmitting source and the receiver, an effective screening of the receiver against direct light is provided.

On the other hand, in case of prior art receivers with a flat application surface the striking of the receiver by direct light is possible even when the pulsemeter is slightly raised from the skin, which can easily take place when the skin is slightly shifted, for example, when the patient feels pain suddenly.

Prior art pulsemeters have also the drawback that when a transparent foil having glue on both sides is used by applying it between the application side and the skin, a particularly large amount of transverse light can strike the receiver. The present invention eliminates this drawback by recessing the foil within the range of the raised portion and by making the height of the raised portion at least equal to the thickness of the foil.

The raised portion preferably consists of a narrow ring enclosing the receiver. When a ring shaped light transmitting source is used with a receiver located in its center it is advantageous to shape the ring as a disk having a flat outer surface and extending concentrically to the light transmitting source.

The invention will appear more clearly from the following detailed description when taken in connection with the accompanying drawings showing by way of example only, a preferred embodiment of the invention idea.

Figure 1:
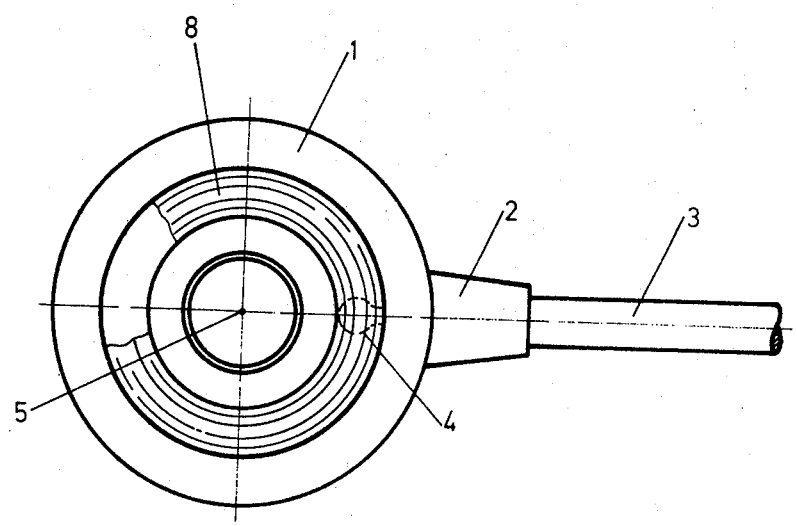
FIG. 1 is a bottom view of the receiver, namely, from the application side.
Figure 2:
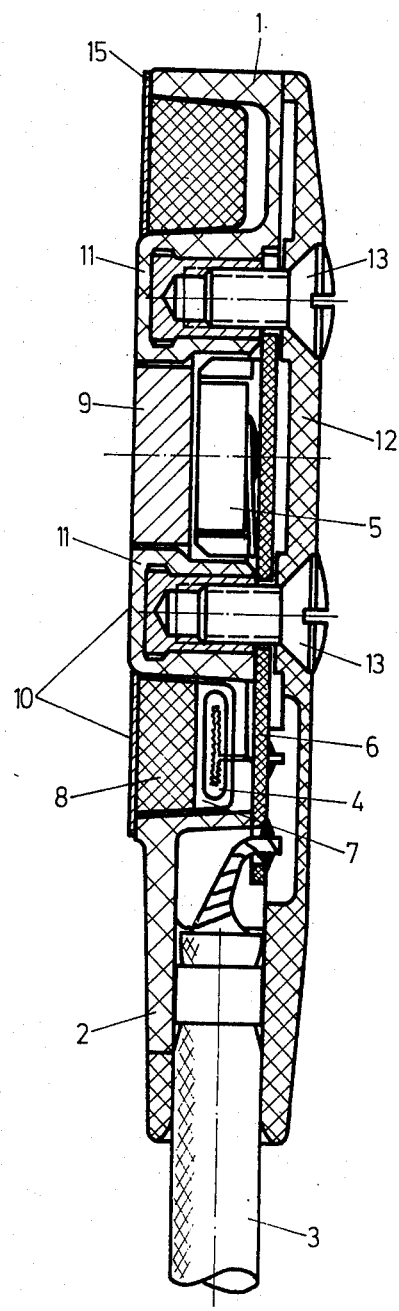
FIG. 2 is a transverse section through the receiver.

The illustrated pulsemeter consists of a round flat carrier 1 of a plastic material provided with a side lug 2. An electrical conduit 3 for a small electrical glow lamp 4 provided in the carier 1, a photo-resistance 5 and a condenser 14, ends in the lug 2. The electrical parts are arranged on a conducting plate 6 in a compressed switching arrangement. The condenser 14 lies parallel to the glow lamp 4 and serves to protect the lamp 4 in case of high frequency dispersions which can take place, for example, during simultaneous use of high frequency chirurgical devices. The small glow lamp 4 lies in a recess 7 of a light transmitting ring 8 of plastic material glued into the carrier 1. The photo-resistance 5 lies in the center 19 of the carrier 1. A light filter 9 is mounted upon the active sensitive side of the photo-resistance 5. The plastic ring 8 consists of polymethylmetacrilate and has a trapeze-like cross-section. When the lamp is switched on, the light is distributed over the plastic ring 8, so that it acts as a light transmitting source. The application side 10 is the one which lies upon the measuring location, which is the skin of the patient. To improve reflection conditions the plastic ring 8 is provided with a reflection layer, for example, a steamed on aluminum layer, upon its side 16 located away from the application side 10 and upon its side walls 17 and 18. This results in a high light output and a practically uniform light thickness. The carrier 1 consists of a plastic material which does not transmit light and is so constructed that the light transmitting source 8 and the receiver 5 are screened relatively to each other in the application plane by a disk-like raised part 11. The side of the carrier located away from the application side 10 is covered by a cover 12 attached by screws 13 to the carrier 1.

The disk-like raised part 11 between the light transmitting source 8 and the receiver 5 amounts to about 0.4 mm.

It may be advantageous to shape the raised part not as a disk, as illustrated but to construct it as a narrow ring.

A transparent foil 15 gluable on both sides is mounted upon the part of the application side 10 which includes te light transmitting source 8. When the applicator is placed upon the human skin surface the higher part 11 of the application side 10 will press more firmly against the skin than the other parts. This will strongly compress the tissue layer located directly under the outer skin surface and having less blood, so that the passage of transverse light is substantially avoided.

As is apparent from the drawing, even if the pulsemeter does not lie completely firmly against the skin, the receiver 5 is screened from direct light by the raised part 11.

Figure 3:
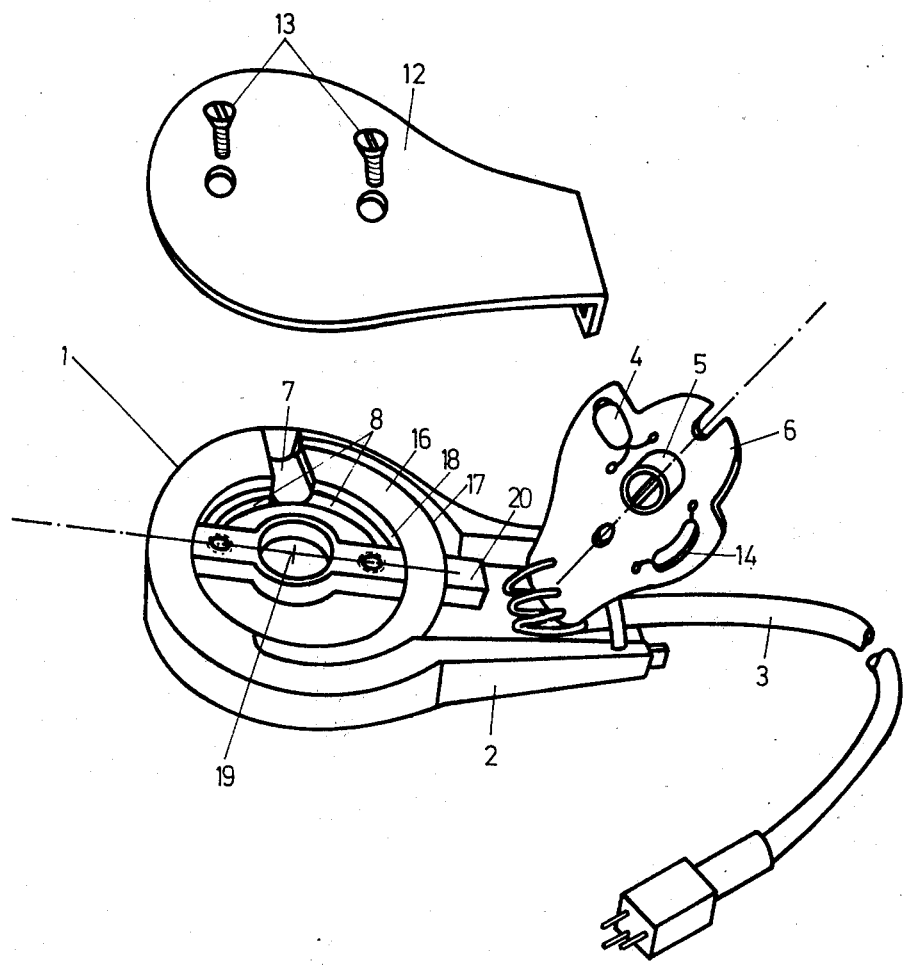
FIG. 3 is a perspective view of the pulsemeter from the side opposite to the application side, the carrier of the electrical parts having been shown open for the sake of clarity.

FIG. 3 shows the conducting plate as being raised and swung upwardly. To facilitate disclosure the conducting plate is shown as being somewhat turned to the viewer. When mounted the central axes indicated by broken lines are in alignment.

The applicator has no metal parts in the application range. The metalized reflection layer at the side walls of the light transmitter reaches only to the height of the application side, so that when high frequency chirurgical devices are used at the same time, no electrical voltages can occur between the applicator and the skin of the patient. Thus the pulsemeter of the present invention is also particularly well suited for taking the pulse during operative treatments with high frequency chirurgical tools. The pulsemeter can be applied to the forehead, cheek or temple of a patient.

What is claimed is:

1. A photoelectric pulsemeter, comprising an applicator having a support member and a supporting plate removably connected with said support member, said support member having an application surface, light transmitting means carried by said support member, a photo-electrical receiver carried by said supporting plate, a lamp carried by said supporting plate and feeding said light transmitting means, said lamp and said receiver fitting functionally to said support member when the applicator is mounted, a supply line having leads attached to the applicator and connected with said lamp and said receiver, and current supplying means connected with said supply line.

2. A pulsemeter according to claim 1, wherein said supporting plate comprises a cover on its outer side.

3. A photoelectric pulsemeter according to claim 1, wherein said support member has an outer surface located opposite said application surface, said supporting plate being mounted upon said outer surface, and a cover covering said supporting plate.

4. A pulsemeter according to claim 3, wherein said cover and said supporting plate constitute a single unit.

5. A pulsemeter according to claim 1, wherein said supporting plate is a printed wiring board having a printed circuit arrangement, said lamp and said receiver being mounted upon said printed circuit arrangement.

6. A pulsemeter according to claim 5, comprising a condenser mounted upon said printed wiring board and electrically connected parallel with said lamp.

7. A pulsemeter according to claim 6, comprising contacts upon said printed wiring board for a removable connection between the supply line and said lamp, said receiver and said condenser carried by said board.

8. A pulsemeter according to claim 7, wherein said contacts are plugs.

9. A pulsemeter according to claim 1, wherein said light transmitting source is a ring-shaped light conductor located coaxially to said receiver and having a recess corresponding to the size of said lamp and located upon its side directed away from the application surface.

10. A pulsemeter according to claim 9, wherein said light conductor is made of a prefabricated plastic material, preferably polymethylmethacrylate and comprises a coating consisting preferably of evaporated on aluminum layer and reflecting light toward the application side, said coating being located upon the side of the light conductor directed away from the application side.

11. A pulsemeter according to claim 10, wherein said coating is also located upon the side walls of said light conductor and extends close to the application side.

12. A pulsemeter according to claim 1, wherein the application surface of said support member has a raised part extending between said light transmitting source and said receiver to screen the receiver from the source.

13. A pulsemeter according to claim 12, wherein said reaised part extends annularly around receiver.

14. A pulsemeter according to claim 12, wherein said light transmitting source is a ring-shaped light conductor located coaxially to said receiver and wherein said raised part is disk-shaped and is located concentrically to said light transmitting source.

15. A pulsemeter according to claim 12, wherein said raised part is about 0.4 mm. high.

16. A pulsemeter according to claim 12, comprising a foil gluable on both sides and having a side extending over the application side, said foil being recessed within the range of said raised part.

* * * * *